(12) United States Patent
Zeller

(10) Patent No.: US 11,241,191 B2
(45) Date of Patent: Feb. 8, 2022

(54) SYSTEMS AND METHODS FOR DETECTING AND CHARACTERIZING PAIN

(71) Applicant: Andru Zeller, Albuquerque, NM (US)

(72) Inventor: Andru Zeller, Albuquerque, NM (US)

( * ) Notice: Subject to any disclaimer, the term of this patent is extended or adjusted under 35 U.S.C. 154(b) by 160 days.

(21) Appl. No.: 16/268,177

(22) Filed: Feb. 5, 2019

(65) Prior Publication Data
US 2019/0239800 A1    Aug. 8, 2019

Related U.S. Application Data

(60) Provisional application No. 62/732,435, filed on Sep. 17, 2018, provisional application No. 62/626,260, filed on Feb. 5, 2018.

(51) Int. Cl.
| | |
|---|---|
| *A61B 5/00* | (2006.01) |
| *A61B 5/01* | (2006.01) |
| *A61B 5/11* | (2006.01) |
| *A61B 5/22* | (2006.01) |
| *G16H 10/60* | (2018.01) |
| *G16H 50/20* | (2018.01) |

(52) U.S. Cl.
CPC .......... *A61B 5/4824* (2013.01); *A61B 5/0053* (2013.01); *A61B 5/0064* (2013.01); *A61B 5/01* (2013.01); *A61B 5/1112* (2013.01); *A61B 5/1114* (2013.01); *A61B 5/227* (2013.01); *A61B 5/486* (2013.01); *A61B 5/6806* (2013.01); *A61B 5/6847* (2013.01); *A61B 5/742* (2013.01); *G16H 10/60* (2018.01); *G16H 50/20* (2018.01); *A61B 2562/0247* (2013.01)

(58) Field of Classification Search
CPC ... A61B 5/4824; A61B 5/0053; A61B 5/6806; A61B 5/0064; G16H 10/60
See application file for complete search history.

(56) References Cited

U.S. PATENT DOCUMENTS

| | | |
|---|---|---|
| 3,156,237 A | 11/1964 | Edmark |
| 3,874,369 A | 4/1975 | Pannier et al. |
| 4,337,780 A | 7/1982 | Metrick |
| 4,505,278 A | 3/1985 | Alban |
| 5,012,817 A | 5/1991 | Zeilinski et al. |
| 5,022,407 A | 6/1991 | Horch et al. |
| 7,854,703 B2 | 12/2010 | Poisner |
| 9,763,618 B2 | 9/2017 | Svensson et al. |
| 2004/0019303 A1* | 1/2004 | Thomson ............ A61B 5/4528 600/595 |

(Continued)

OTHER PUBLICATIONS

International Search Report and Written Opinion issued for PCT/US19/16661, dated Apr. 30, 2019, 11 pp.

*Primary Examiner* — Gary Jackson
*Assistant Examiner* — Zahed Kabir
(74) *Attorney, Agent, or Firm* — Zeller IP Group, PLLC; Kyle M. Zeller

(57) ABSTRACT

Various systems are disclosed herein for detecting, monitoring, evaluating, and characterizing pain. They systems include a number of connected components, such as a provider device, a body-mapping system, a patient device, a user device, a referred pain device and/or a rectal probe device. Accordingly, the systems allow providers to track location-specific pain intensity for any number of patients over time in order to generate reports and determine treatment recommendations for such patients.

14 Claims, 8 Drawing Sheets

(56) References Cited

U.S. PATENT DOCUMENTS

| | | |
|---|---|---|
| 2006/0122542 A1 | 6/2006 | Smith et al. |
| 2006/0129068 A1 | 6/2006 | Makosinski et al. |
| 2007/0287991 A1* | 12/2007 | McKay .............. A61B 5/14546 |
| | | 604/892.1 |
| 2008/0051638 A1 | 2/2008 | Iliff |
| 2008/0097236 A1 | 4/2008 | Kuban |
| 2009/0005649 A1* | 1/2009 | Baird .................... A61B 5/7475 |
| | | 600/300 |
| 2011/0066078 A1* | 3/2011 | Sarvazyan ............... A61B 5/16 |
| | | 600/587 |
| 2011/0071419 A1* | 3/2011 | Liu ...................... A61B 5/0053 |
| | | 600/547 |
| 2011/0082384 A1 | 4/2011 | Harte et al. |
| 2012/0130202 A1 | 5/2012 | Jain |
| 2014/0275846 A1 | 9/2014 | Fitzgerald et al. |
| 2016/0015272 A1* | 1/2016 | Gaddipati ............ A61B 5/4827 |
| | | 600/557 |
| 2016/0034664 A1* | 2/2016 | Santos ................... G16H 10/60 |
| | | 705/3 |
| 2017/0071481 A1* | 3/2017 | Xie ...................... A61B 5/0002 |
| 2017/0340264 A1 | 11/2017 | Gregersen et al. |

* cited by examiner

SYSTEMS AND METHODS FOR DETECTING AND CHARACTERIZING PAIN

CROSS-REFERENCE TO RELATED APPLICATIONS

This specification claims benefit of U.S. provisional patent application Ser. No. 62/626,260, titled "Systems and Methods for Detecting and Characterizing Pain," filed Feb. 5, 2018, and U.S. provisional patent application Ser. No. 62/732,435, titled "Systems and Methods for Detecting and Characterizing Pain," filed Sep. 17, 2018. Each of the above applications is incorporated by reference herein in its entirety.

BACKGROUND

This specification relates generally to pain management and, more specifically, to systems and methods that allow providers to detect and evaluate pain experienced by patients.

Despite significant achievements in nearly every other area of medicine over the past few decades, pain management has proven elusive to technological advances. Indeed, the detection and characterization of pain remains a subjective exercise, where clinicians and pain management practitioners must rely on their patients to self-report the location and intensity of their pain.

In practice, practitioners often ask patients to rate their pain, such as on a scale ranging from 1 to 10 or on a scale that includes emojis ranging from a sad face to a happy face. Unfortunately, pain scales cannot account for the fact that each person has a unique psychological and biological relationship to pain. Moreover, such scales only allow practitioners to assess a patient's overall experience of pain—these methods do not provide an objective indication of the location of pain nor do they allow for scientific comparison of a particular patient's pain over time.

Accordingly, it is difficult for physicians to focus on certain areas for pain reduction, particularly when a patient suffers from chronic pain. It is further difficult for physicians to recommend meaningful changes in, for example, a patient's lifestyle, diet, medication, therapies, etc., because practitioners are unable to objectively monitor patient progress (e.g., pain reduction) over time.

There remains a need for systems and methods that allow pain management practitioners to measure and evaluate patients' pain in a systematic, calibrated and reproducible format that can be tracked over time. It would be beneficial if such systems and methods allowed providers to measure pain topographically and view results in a graphical format, such as a two-dimensional ("2D") or three-dimensional ("3D") model of a patient's body. It would be further beneficial if such systems and methods could determine customized treatment recommendations for patients, for example, based on tracked pain information and identified pain patterns.

SUMMARY

In accordance with the foregoing objectives and others, exemplary methods and systems are disclosed herein to allow providers to detect, monitor, evaluate and/or characterize pain experienced by one or more patients. The disclosed systems and methods may employ standards of measurement that allow for calibration for a single patient and/or among a plurality of patients. Such systems may be adapted to determine and record location-specific pain intensity for any number of patients, at one or more times, by employing various components, such as a provider device, a referred pain device, a rectal probe, a body-mapping system and/or a patient device.

In one embodiment, a system is provided. The system may include a provider device operated by a provider, the provider device adapted to measure pressure information relating to a force applied, by the provider, to a location on a body of a patient. The system may also include a body-mapping system adapted to determine location information relating to the location of the applied force; a patient device operated by the patient, the patient device adapted to determine feedback information relating to an intensity of pain experienced by the patient due to the applied force; and a server in communication with the provider device, the body-mapping system and the patient device via a network. The server may be adapted to receive the pressure information from the provider device, the location information from the body-mapping system, and/or the feedback information from the patient device. The server may be further adapted to store, in a memory, pain information including the pressure information, the location information and the feedback information. And the server may be adapted to generate one or more reports, each including a graphical representation of some or all of the pain information (e.g., a 2D or 3D body map).

In certain embodiments, the pressure information may include a magnitude of the applied force, a start time of the applied force and/or an end time of the applied force. And the location information may include one or more of a direction of the applied force, an area over which the force is applied to the location, and a depth within the location to which the force is applied.

Optionally, the server may be adapted to determine a treatment recommendation for the patient based on the pain information. Such treatment recommendation may relate, for example, to a medication, an exercise, a stretch, a diet and/or sleep.

In another embodiment, a method for determining and characterizing pain is provided. The method may include receiving first session information including: receiving first location information (e.g., from a body-mapping system) representing a location on a patient's body upon which a provider asserts pressure at a first time; receiving first pressure information (e.g., from a provider device) representing an amount of pressure asserted by the provider at the first time; and receiving first feedback information (e.g., from a patient device) representing an intensity of pain experienced by the patient at the first time. The method may further include storing the first session information and associating such information with patient information corresponding to the patient. The method may include repeating the above steps at any number of additional times during the first session, while varying or maintaining the location and/or magnitude of pressure applied to the patient. Moreover, the method may optionally include determining and displaying a graphical representation of any or all of the first session information, for example via a 2D or 3D body map, which may be displayed on a user device.

Generally, the above method may further include determining a treatment recommendation, based on the first session information, and providing the same to the patient and/or the provider. The method may, additionally or alternatively, include: treating the patient in accordance with the treatment recommendation and receiving second session information. Second session information may include, for example, second location information (e.g., from a body-mapping system) representing a location on a patient's body upon which a provider asserts pressure at a second time; second pressure information (e.g., from a provider device) representing an amount of pressure asserted by the provider at the second time; and second feedback information (e.g., from a patient device) representing an intensity of pain experienced by the patient at the second time. The method may further include storing the second session information and associating such information with patient information corresponding to the patient. The method may include repeating the above steps at any number of additional times during the second session, while varying or maintaining the location and/or magnitude of pressure applied to the patient. In this embodiment, the method may further include comparing/contrasting the first session information and the second session information. The method may optionally include: determining an efficacy of the first treatment, based on said comparing/contrasting; determining a second treatment recommendation, based on said comparing/contrasting; determining whether the patient is accurately reporting their symptoms, based on said comparing/contrasting; and/or determining and displaying a second graphical representation of any or all of the first session information and the second session information.

In certain embodiments, the location information may additionally or alternatively include determining a patient's position, which may change throughout a given session.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Various methods, systems and apparatuses are disclosed herein that allow for providers to detect, monitor, evaluate and/or characterize pain experienced by patients. Such embodiments may be adapted to determine and record location-specific pain intensity information for any number of patients, at one or more times. The disclosed embodiments may improve on currently available tools for assessing and tracking a patient's level of pain by isolating and determining painful locations, recording pain characteristics over time and/or providing a visual representation of such pain (e.g., in the form of a body map).

The disclosed embodiments may utilize various information to determine and/or characterize patient pain, such as: patient information, patient feedback information (e.g., an indication of the intensity of pain experienced by a patient at a given time), location information (e.g., a location upon which pressure is exerted by a provider at the given time), pressure information (e.g., a magnitude and/or direction of the force exerted by the provider at the given time) and temperature information (e.g., temperature as recorded at the point of examination by a provider device). Accordingly, the embodiments may employ various components, such as a provider device, a rectal probe device, a referred pain device, a body-mapping system and/or a patient device.

Exemplary embodiments may allow researchers to perform targeted research into pain treatments (e.g., chronic pain treatments), which may positively affect research into medications, technologies and manual techniques. The disclosed embodiments may also allow for comparison of different approaches to pain management to establish best practices. Additionally or alternatively, various embodiments described herein may allow providers to more accurately determine the truthfulness of a patient's reported pain symptoms in order to determine an appropriate treatment.

The described embodiments may also help clinicians make an initial diagnosis for chronic pain illnesses (e.g., Fibromyalgia, non-cardiac chest pain, tension headaches, etc.) by standardizing diagnostic criteria based on pain location and/or pressure ranges. The embodiments may also assist clinicians in better determining the precise location of pain in complex medical decision-making like urgent care and/or emergency room evaluations of abdominal pain. For example, the described embodiments may be used by clinicians to accurately differentiate the location and depth of abdominal pain. The embodiments described herein may thus allow clinicians to differentiate between superficial, muscular pain and deeper, organ-based pain by approaching an exam with a 3D perspective.

System

Figure 1:
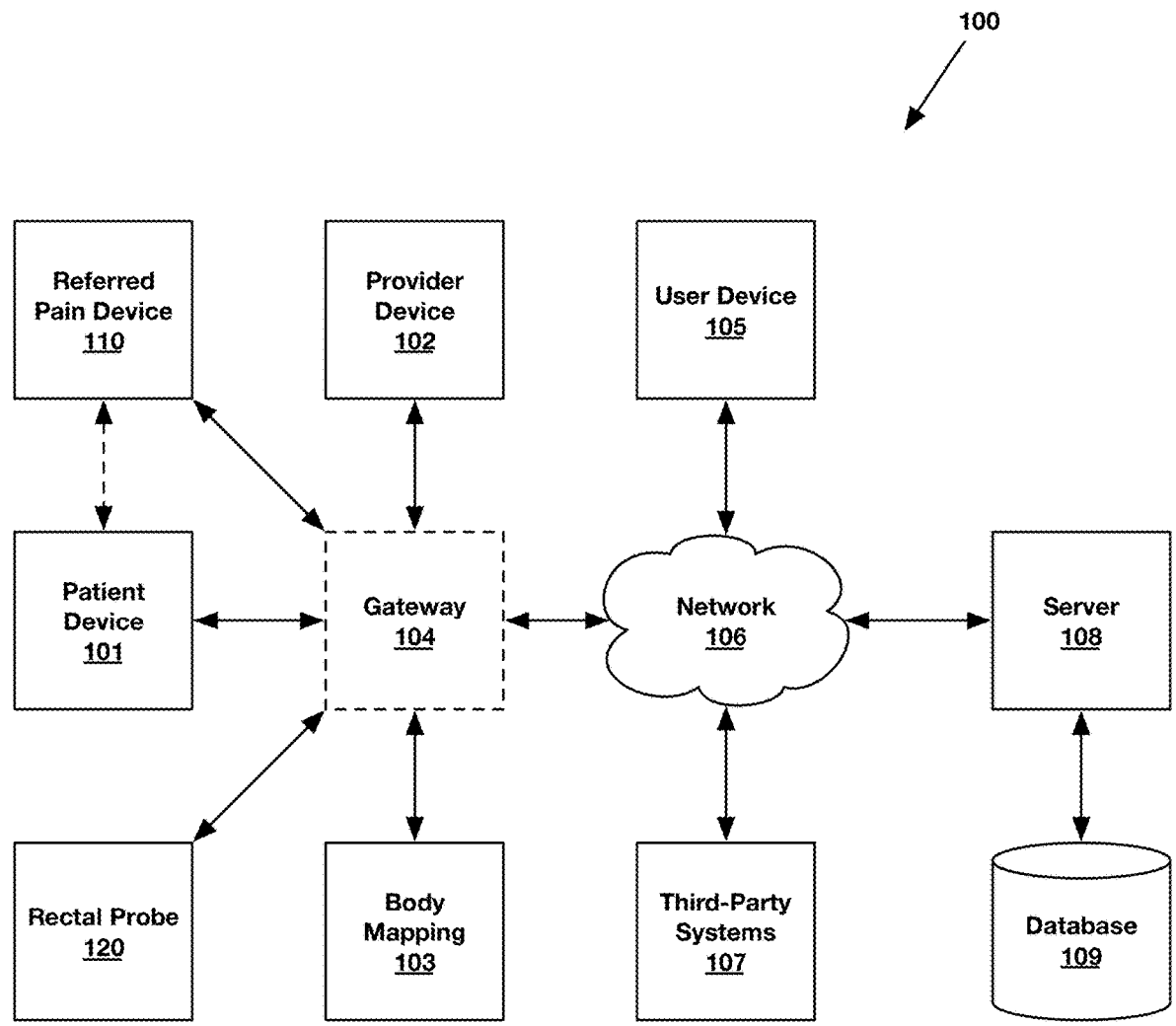
FIG. 1 shows a block diagram of an exemplary system 100 for detecting and characterizing pain in accordance with one or more embodiments presented herein.

Referring to FIG. 1, a block diagram of an exemplary system for detecting and characterizing pain according to an embodiment is illustrated. As shown, the system may include a patient device 101, a provider device 102, a referred pain device 110, a rectal probe device 120, and/or a body-mapping system 103, each of which may be in communication with a network 106 (e.g., Internet, intranet, local-area network ("LAN"), wide-area network ("WAN"), cellular, etc.). One or more of the patient device 101, provider device 102, referred pain device 110, rectal probe 120, and/or body-mapping system 103 may additionally or alternatively be in communication with a gateway 104.

The system may comprise a server 108 in communication with the network 106 and/or the gateway 104. The server 108 may be adapted to receive, determine, record and/or transmit patient information for any number of patients and provider information for any number of providers. Such information may be manually entered and/or selected by a user via an online, mobile or desktop client application running on a user device 105. Patient information may additionally or alternatively be automatically received from any number of patient devices 101, provider devices 102, referred pain devices 110, rectal probes 120, and/or body-mapping systems 103 (either directly or indirectly via an intermediate device). The server may store received or determined information in, for example, a database 109 (e.g., continuously and/or at predetermined time intervals). In one embodiment, the database 109 may employ File-Maker Pro™ or other database software.

Generally, provider information may include, but is not limited to: provider identification information (e.g., name, age, date of birth, sex, social security number, unique ID, photo, employer, medical license number(s), etc.); contact information (e.g., email address, physical address, phone number, etc.); billing information (e.g., credit card information, billing address, insurance accepted, etc.); and/or any number of patients associated with the provider.

Patient information may include, but is not limited to: patient identification information (e.g., name, age, date of birth, sex, social security number, unique ID, photo, etc.); contact information (e.g., email address, physical address, phone number, etc.); consent information (e.g., scanned consent forms and/or recorded dates of consent forms for use of the provider device and/or for sharing medical information relating to the use thereof); billing information (e.g., credit card information, billing address, etc.); insurance information (e.g., insurance provider, plan, type, benefits, member number, group number, etc.); current and/or historical medical information (e.g., illnesses, injuries, types of medications taken, dosage to be taken, days and/or times when such medication should be taken, physical therapy routines, radiological studies, reported symptoms etc.); and/or pain information (discussed below). Patient information may also include information relating to third parties associated with the patient (e.g., a doctor or other health care provider who may conduct a pain measurement session and/or users who may access patient information associated with the patient).

Generally, pain information may include, but is not limited to: pressure information relating to manual pressure applied, by a provider, to a location on the patient's body at given time(s) during a pain measurement session (e.g., force applied, start time, end time, duration, depth, vector of force applied, etc.); location information relating to the location(s) on the patient's body where the provider applies pressure during a given pain measurement session (e.g., body part, specific point(s) on a body part, patient position, start time, end time, duration, vector of force applied in relation to the patient's anatomy, etc.); feedback information relating to the intensity of pain felt by a patient when the provider provides a stimulus and/or applies pressure to a location on the patient's body during a pain measurement session (e.g., pain intensity, start time, end time, duration, etc.); temperature information relating to the temperature and/or changes in temperature of the location(s) on the patient's body where the provider provides a stimulus and/or applies pressure during a pain measurement session; and/or any number of reports associated with a patient (e.g., graphical reports such as 2D or 3D body maps (discussed below), charts, graphs, textual reports and/or treatment recommendations).

In certain embodiments, some or all of the pain information may be associated with session information relating to one of a number of pain measurement sessions. Session information may include, but is not limited to: a patient for whom a pain measurement session is conducted, a provider who conducted the session, a number of sessions conducted for the patient, a session number, a unique session identifier (e.g. session ID), patient position during a session, date of a session, start time, end time, duration, provider notes, session plan information (discussed below) and/or others.

Notification information, such as notification events and/or notification content, may also be stored in the database 109. The system may be adapted to provide notifications to providers (e.g., via a user device 105). Generally, the system is configured to automatically transmit notifications to providers based on predefined, rule-based events stored in the database 109. For example, providers may be notified when a target pressure and/or a duration has been reached during a pain measurement session and/or when a report or treatment suggestion has been created by the system. Such notifications may be in the form of a visual alert, an audio alert, or a message (e.g., a push message, an SMS message or email) sent to a user device 105 and/or provider device 102.

As shown, the system may also include one or more user devices 105. Generally, a user device 105 may be any device capable of running a client application and/or of accessing the server 108 (e.g., via a network 106) to allow providers or other users to create, access, update and/or delete patient information, provider information and/or notification information. Such configuration may allow users of the user device/client application to input information and/or interact with the server from any location. Exemplary user devices may include general-purpose computers, special-purpose computers, desktop computers, laptop computers, smartphones, tablets and/or wearable devices.

In certain embodiments, the user device 105 may be adapted to receive, determine, record and/or transmit patient information, including real-time and/or historical pain information. The patient information may be received from and/or transmitted to the server 108 (e.g., a server application running on the server) or a separate client application. Moreover, any of such patient information may be stored in and/or retrieved from one or more local or remote databases 109.

Exemplary client applications may allow a provider and/or patient to input patient information, such as patient identification information, and/or any pain information relating to one or more pain measurement sessions. A provider may also view, create, update and/or delete notification information, such as the type of notification desired and any rules to trigger such notifications. A provider may also input a particular sequence of notifications, e.g., visual notification first, then an audio notification, and finally an SMS notification. After the patient information and/or notification information has been created, such information may be sent to the server.

In some embodiments, a client application running on a user device 105 may be adapted to allow a provider to create, update and/or delete one or more pain measurement session plans. Each plan may comprise target pressures, target locations and/or target durations relating to a particular pain measurement session. Such information may be transmitted to the server 108 and stored in the database 109.

After a pain measurement session plan has been created, the session information may be displayed to the provider (e.g., via the user device 105 and/or the provider device 102). In one embodiment, the provider device 102 may employ such information to notify the provider if they deviate from the plan.

Additionally or alternatively, the client application may be adapted to determine a treatment plan for one or more patients. In such embodiments, the client application may allow the provider to input medication information and/or therapy information for the treatment plan, such as the name of the user, a medication name, a therapy name and/or description, the times of the scheduled doses/therapies, the length of the regimen, etc. Such information may be stored by the server and may be employed to create any number of reports that may be viewed by the provider and/or transmitted to the patient (e.g., via printing of the report or electronically sending the same to the patient).

As shown in FIG. 1, the system may further comprise a provider device 102. As discussed in detail below with reference to FIG. 3, the provider device 102 may be adapted to determine pressure information relating to manual manipulation of a patient, by a provider, during one or more pain measurement sessions. The provider device 102 may be further adapted to transmit such pressure information to the server 108 directly or indirectly via the gateway 104 and/or the network 106 (e.g., using Wi-Fi, Ethernet, Bluetooth, Bluetooth Low Energy ("BLE"), Near Field Communication ("NFC"), Radio Frequency ID ("RFID"), ZIGBEE, Z Wave, Code Division Multiple Access ("CDMA") and/or Global Signal for Mobiles ("GSM")).

In certain embodiments, the system 100 may further comprise a body-mapping system 103. As discussed in detail below with reference to FIG. 4, the body-mapping system 103 may be adapted to determine location information during one or more pain measurement sessions. The body-mapping system 103 may be further adapted to transmit such location information to the server 108 directly or indirectly via the gateway 104 and/or the network 106 (e.g., using Wi-Fi, Ethernet, Bluetooth, BLE, NFC, RFID, ZIGBEE, Z Wave, CDMA and/or GSM).

The system may include a patient device 101, which is adapted to determine feedback information from a patient throughout one or more pain measurement sessions. The patient device 101 may be further adapted to transmit such feedback information to the server 108 directly or indirectly via the gateway 104 and/or the network 106 (e.g., using Wi-Fi, Ethernet, Bluetooth, BLE, NFC, RFID, ZIGBEE, Z Wave, CDMA and/or GSM). Patient devices are discussed in detail below with reference to FIGS. 5-6.

In one embodiment, the system may comprise a rectal probe device 120. As discussed in detail below with reference to FIGS. 8-9, the rectal probe device 120 may be adapted to determine sensor information and/or sphincter muscle tone information during one or more pain measurement sessions. The rectal probe device 120 may be further adapted to transmit such information to the server 108 directly or indirectly via the gateway 104 and/or the network 106 (e.g., using Wi-Fi, Ethernet, Bluetooth, BLE, NFC, RFID, ZIGBEE, Z Wave, CDMA and/or GSM).

In certain embodiments, the system may include a referred pain device 110 that is adapted to track referred pain (i.e., pain which has an origin and then "travels" to a different destination in the body). As discussed in detail below, such device may be adapted to receive referred pain information from a patient, wherein the referred pain information represents an indication of the location(s) on a patient's body where pain is experienced at any given time during a pain measurement session.

The system may optionally include a gateway 104 that is adapted to receive information from one or more of the provider device 102, patient device 101, referred pain device 110, rectal probe 120, and/or body-mapping system 103 (e.g., via Bluetooth, BLE, NFC, RFID, ZIGBEE, Z Wave, CDMA and/or GSM) and transmit such information to the server 108 (e.g., via the network 106). The gateway 104 may be further adapted to receive information from the server 108 (e.g., via Wi-Fi and/or Ethernet) and transmit such information to one or more of the provider device 102, patient device 101, referred pain device 110, rectal probe 120, and/or body-mapping system 103 (e.g., via Bluetooth, BLE, NFC, RFID, ZIGBEE, Z Wave, CDMA and/or GSM).

In an alternative embodiment, the functionality of the gateway 104 may be incorporated into a user device 105. In this embodiment, one or more of the provider device 102, patient device 101, referred pain device 110, rectal probe 120, and/or body-mapping system 103 may be configured to communicate with the user device 105 through a wireless protocol (e.g., Bluetooth or BLE) and the user device may be configured to communicate with the server 108 through a wireless protocol (e.g., Wi-Fi or cellular). Using a user device, a provider may view and/or update patient information (e.g., pain information) received from one or more of the provider device, patient device, referred pain device, rectal probe, body-mapping system and/or server in communication with the user device (e.g., via a client application installed on the user device and/or via a web application accessed by the user device).

Optionally, the server 108 may be connected to one or more third-party systems 107 via the network 106. Third-party systems 107 may store information in one or more databases that may be accessed by the server. Generally, third-party systems may include, but are not limited to: electronic medical/health record systems, Global Positioning Systems ("GPS"); patient management systems, medical imaging systems, telemedicine systems, other healthcare provider systems, calendaring and/or scheduling systems, backup systems, billing systems, communication systems and/or others.

The server 108 may be capable of retrieving and/or storing information from third-party systems 107, with or without user interaction. Moreover, the server may be capable of transmitting stored information to third-party systems.

Server

Figure 2:
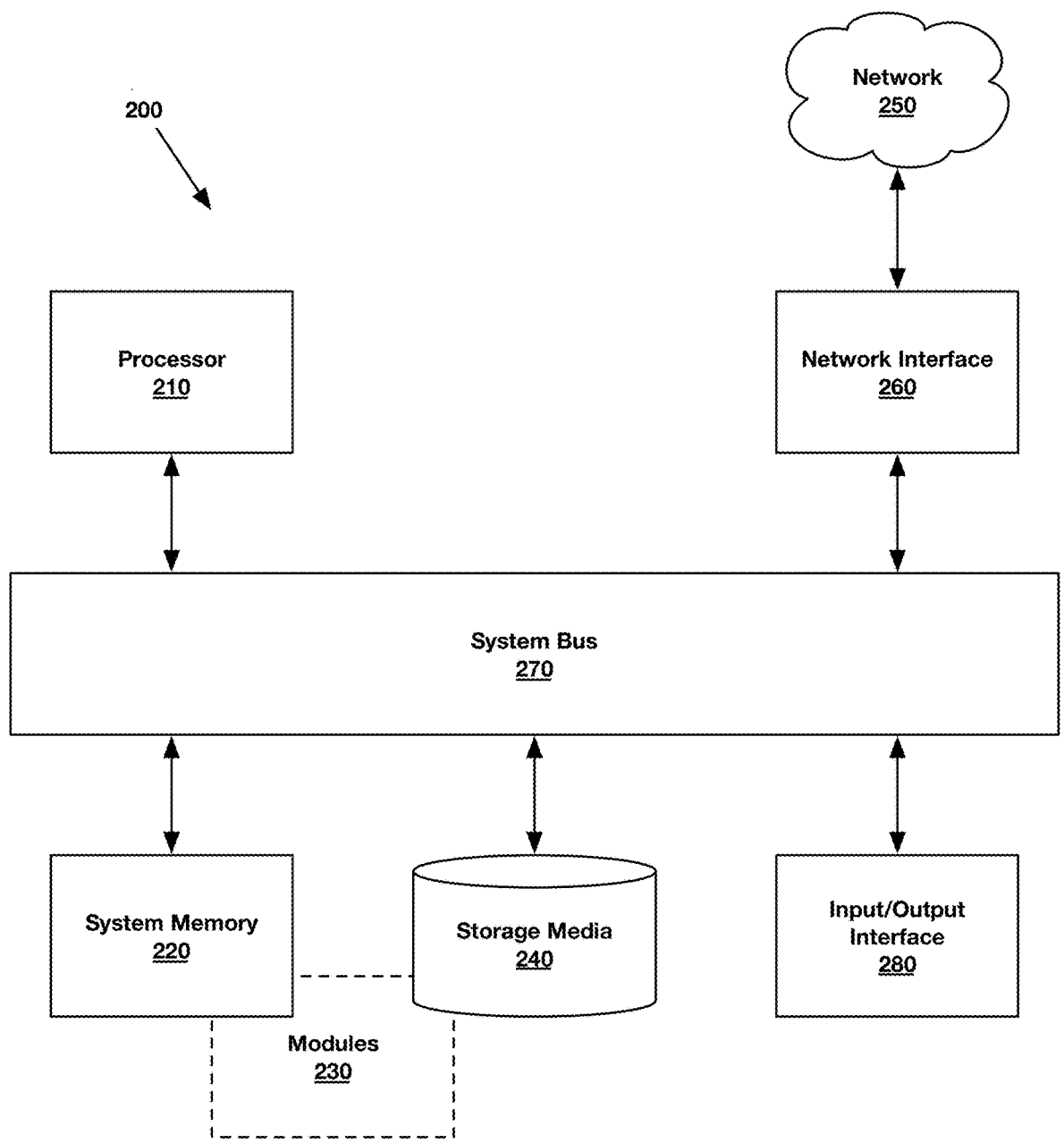
FIG. 2 shows a block diagram of an exemplary server 200 in accordance with one or more embodiments presented herein.

Referring to FIG. 2, a block diagram is provided illustrating a server 200 and modules 230 in accordance with one or more embodiments presented herein. The server 200 may correspond to any of the various computers, servers, mobile devices, embedded systems, or computing systems presented herein. The modules 230 may comprise one or more hardware or software elements configured to facilitate the server 200 in performing the various methods and processing functions presented herein.

As shown, the server 200 may include various internal and/or attached components such as a processor 210, a system bus 270, system memory 220, storage media 240, an input/output interface 280, and a network interface 260 for communicating with a network 250. The server 200 may be implemented as a conventional computer system, an embedded controller, a laptop, a server, a mobile device, a smartphone, a set-top box, over-the-top content TV ("OTT TV"), Internet Protocol television ("IPTV"), a kiosk, one or more processors associated with a display, a customized machine, any other hardware platform and/or combinations thereof. And, in some embodiments, the server 200 may be a distributed system configured to function using multiple servers interconnected via a data network or system bus 270.

The processor 210 may be configured to execute code or instructions to perform the operations and functionality described herein, manage request flow and address mappings, and to perform calculations and generate commands. Generally, the processor 210 may be configured to monitor and control the operation of the components in the server 200. To that end, the processor 210 may be a general-purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 210 may be a single processing unit, multiple processing units, a single processing core, multiple processing cores, special purpose processing cores, coprocessors, or any combination thereof. According to certain embodiments, the processor and/or other components of the server may be a virtualized server executing within one or more other servers.

The system memory 220 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 220 also may include volatile memories, such as random-access memory ("RAM"), static random-access memory ("SRAM"), dynamic random-access memory ("DRAM"), and synchronous dynamic random-access memory ("SDRAM"). Other types of RAM also may be used to implement the system memory. The system memory 220 may be implemented using a single memory module or multiple memory modules. While the system memory is depicted as being part of the server 200, one skilled in the art will recognize that the system memory may be separate from the server without departing from the scope of the subject technology. It should also be appreciated that the system memory 220 may include, or operate in conjunction with, a non-volatile storage device such as the storage media 240.

The storage media 240 may include a hard disk, a compact disc read-only memory ("CD-ROM"), a digital versatile disc ("DVD"), a Blu-ray disc, a magnetic tape, a flash memory, other non-volatile memory device, a solid-state drive ("SSD"), any magnetic storage device, any optical storage device, any electrical storage device, any semiconductor storage device, any physical-based storage device, any other data storage device, or any combination or multiplicity thereof. The storage media 240 may store one or more operating systems, application programs and program modules such as module, data, or any other information. The storage media 240 may be part of, or connected to, the server 200. The storage media may also be part of one or more other servers that are in communication with the server such as other computers, database servers, cloud storage, network attached storage, and so forth.

The modules 230 may comprise one or more hardware or software elements configured to facilitate the server 200 with performing the various methods and processing functions presented herein. The modules 230 may include one or more sequences of instructions stored as software or firmware in association with the system memory 220, the storage media 240, or both. The storage media 240 may therefore represent examples of machine or computer-readable media on which instructions or code may be stored for execution by the processor. Machine or computer-readable media may generally refer to any medium or media used to provide instructions to the processor. Such machine or computer-readable media associated with the modules may comprise a computer software product. It should be appreciated that a computer software product comprising the modules may also be associated with one or more processes or methods for delivering the module to the server via the network, any signal-bearing medium, or any other communication or delivery technology. The modules 230 may also comprise hardware circuits or information for configuring hardware circuits such as microcode or configuration information for an FPGA or other PLD.

The input/output ("I/O") interface 280 may be configured to couple to one or more external devices, to receive data from the one or more external devices, and to send data to the one or more external devices. Such external devices along with the various internal devices may also be known as peripheral devices. The I/O interface 280 may include both electrical and physical connections for operably coupling the various peripheral devices to the server 200 or the processor 210. The I/O interface 280 may be configured to communicate data, addresses, and control signals between the peripheral devices, the server, or the processor. The I/O interface 280 may be configured to implement any standard interface, such as small computer system interface ("SCSI"), serial-attached SCSI ("SAS"), fiber channel, peripheral component interconnect ("PCP"), PCI express (PCIe), serial bus, parallel bus, advanced technology attachment ("ATA"), serial ATA ("SATA"), universal serial bus ("USB"), Thunderbolt, FireWire, various video buses, and the like. The I/O interface may be configured to implement only one interface or bus technology. Alternatively, the I/O interface may be configured to implement multiple interfaces or bus technologies. The I/O interface may be configured as part of, all of, or to operate in conjunction with, the system bus 270. The I/O interface 280 may include one or more buffers for buffering transmissions between one or more external devices, internal devices, the server 200, or the processor 210.

The I/O interface 280 may couple the server 200 to various input devices including mice, touch-screens, scanners, biometric readers, electronic digitizers, sensors, receivers, touchpads, trackballs, cameras, microphones, keyboards, any other pointing devices, or any combinations thereof.

The I/O interface 280 may also couple the server 200 to various output devices including display devices, speakers, printers, tactile-feedback devices, automation control, robotic components, actuators, motors, fans, solenoids, valves, pumps, transmitters, signal emitters, lights, and so forth. Exemplary display devices include, but are not limited to one or more of: projectors, cathode ray tube ("CRT") displays, liquid crystal displays ("LCD"), light-emitting diode ("LED") displays and/or organic light-emitting diode ("OLED") displays.

The server 200 may operate in a networked environment using logical connections through the network interface 260 to one or more other systems or servers 200 across the network 250. The network 250 may include WANs, LANs, intranets, the Internet, wireless access networks, wired networks, mobile networks, telephone networks, optical networks, or combinations thereof. The network 250 may be packet switched, circuit switched, of any topology, and may use any communication protocol. Communication links within the network 250 may involve various digital or an analog communication media such as fiber optic cables, free-space optics, waveguides, electrical conductors, wireless links, antennas, radio-frequency communications, and so forth.

The processor 210 may be connected to the other elements of the server 200 or the various peripherals discussed herein through the system bus 270. It should be appreciated that the system bus 270 may be within the processor, outside the processor, or both. According to some embodiments, any of the processor 210, the other elements of the server 200, or the various peripherals discussed herein may be integrated into a single device such as a system on chip ("SOC"), system on package ("SOP"), or ASIC device.

In one embodiment, the server 200 may comprise a server application configured to receive, determine, and/or transmit patient information, provider information and/or notification information. As discussed above, the received patient information may comprise pain information, such as pressure information, location information and/or feedback information. Accordingly, the server application may employ received information to determine a patient's response to pressure(s) applied to one or more locations on the patient's body by a provider. For example, the server application may determine that a certain pressure was applied to a specific location on a patient's body at a given time and, in response to that pressure, the patient provided the received feedback information relating to the intensity of pain felt at the given time.

The server may keep track of a patient's pain information over any number of sessions and prepare, display and/or transmit reports regarding the patient to the provider (e.g., via user device). In one embodiment, such reports may be in a graphical format, such as a 2D or 3D body map. Additionally or alternatively, such reports may include one or more of: a treatment recommendation, a prognosis, a diagnosis, a comparison of pain information received at different times, and/or a determination as to whether the patient is accurately reporting their symptoms.

In one embodiment, the server 200 may engage in communication with a user device (FIG. 1 at 105) via a web browser or similar client application running on the user device. For example, a client application running on the user device may make a request for a specific resource using HTTP/HTTPS and the server may respond with the content of that resource or an error message if unable to do so. The resource may be data or a file stored in a database. The server can receive content from a user, possibly using HTTP/HTTPS.

Generally, a client application may be adapted to present various user interfaces to users. Such user interfaces may be based on patient information, provider information and/or notification information stored on the user device and/or received from the server. Accordingly, each client application may comprise HTML data, images, videos, icons, and/or executable code. The executable code may be composed in JavaScript, ECMAScript, coffeescript, python, Ruby or any other programming languages suitable for execution within the pain management application or for translation into an executable form.

In one embodiment, communication between a client application and a server application running on the server may involve the use of a translation and/or serialization module. A serialization module can convert an object from an in-memory representation to a serialized representation suitable for transmission via HTTP or another transport mechanism. For example, the serialization module may convert data from a native Python, Ruby, or Java in-memory representation into a JSON string for communication over the client-to-server transport protocol. After the JSON string is received by the receiver, a de-serialization module may convert the JSON string back into the native Python, Ruby, or Java in-memory representation for use by the client application or the patient monitoring and management application.

It will be apparent to one of ordinary skill in the art that, in certain embodiments, any of the functionality of the server may be incorporated into a client, and vice versa. Likewise, any functionality of a client application may be incorporated into a browser-based client, and such embodiments are intended to be fully within the scope of this disclosure. For example, a browser-based client application could be configured for offline work by adding local storage capability, and a native application could be distributed for various native platforms via a software layer that executes the browser-based program on the native platform.

Provider Device

Figure 3:
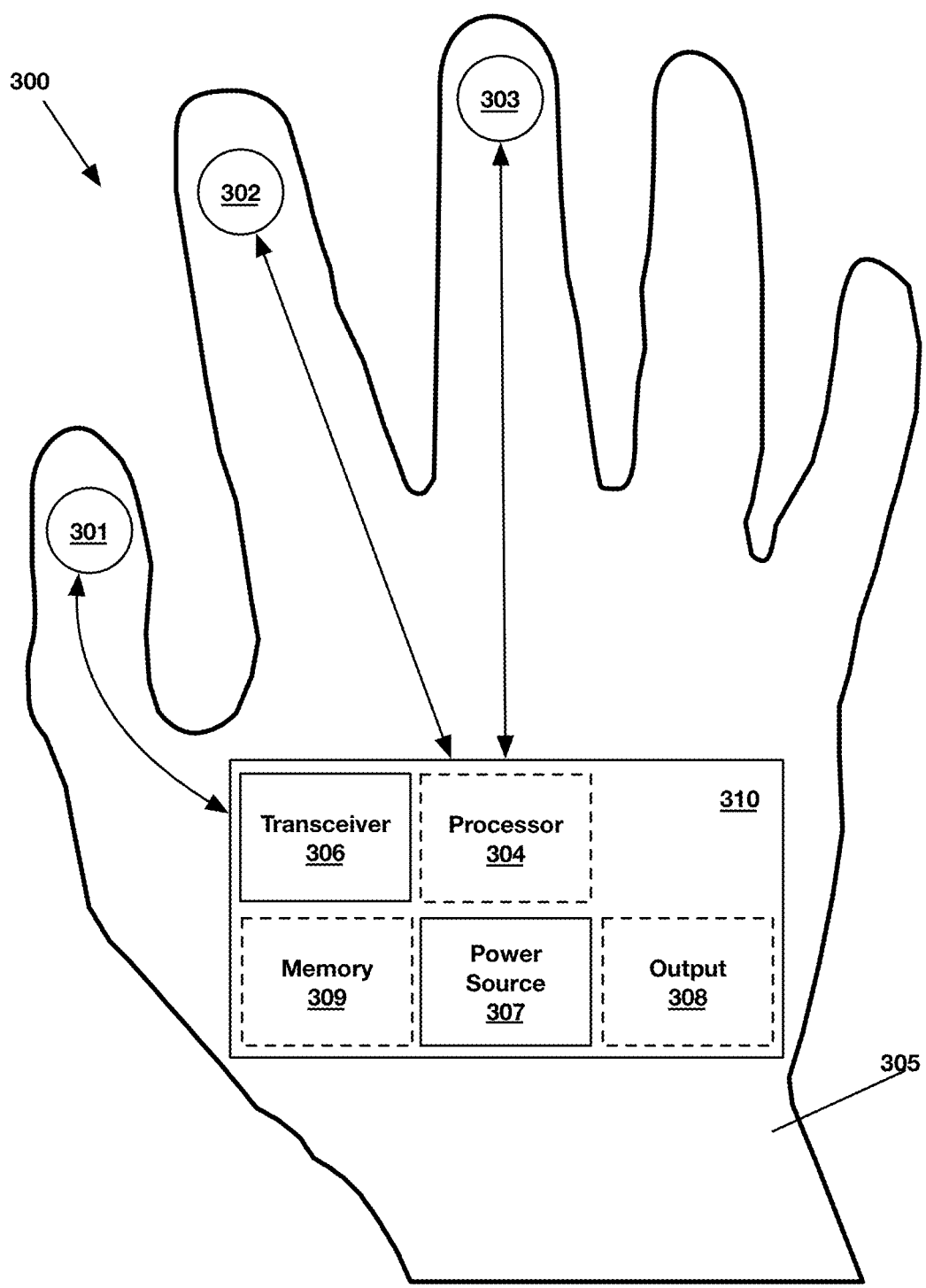
FIG. 3 shows an exemplary provider device 300 in accordance with one or more embodiments presented herein.

Referring to FIG. 3, an exemplary provider device 300 is illustrated. The provider device 300 may be employed by a provider to apply pressure (e.g., via manual manipulation) to any number of locations on a patient's body during one or more pain measurement sessions. The provider device 300 may determine pressure information (e.g., the magnitude of the applied pressure, a start time, an end time, a depth, an area, a duration, a vector of applied force, etc.) and transmit this information to the server and/or user device(s).

As shown, the provider device 300 may comprise a glove 305 that may be worn on a hand of the provider. Generally, the glove 305 may be adapted to allow for unencumbered movement during patient examination and an unobstructed sense of touch throughout the palm and fingers. To that end, the glove 305 may be made from one or more of the following materials: latex, nitrile rubber, polyvinyl chloride, neoprene, polyester, leather, polyurethane, cotton and/or rayon. The glove may be unpowdered, or powdered with cornstarch for lubrication.

In one embodiment, the provider device 300 may be used to directly contact a patient's skin. In other embodiments, a medical glove or other protective covering may be employed over the provider device to prevent the provider device from directly contacting a patient's skin. In either case, the provider device may be either reusable and/or washable, or may be disposable.

The provider device 300 may comprise a number of sensors 301-303 disposed within the glove 305 or on the outer surface thereof. The tactile sensors 301-303 may determine pressure applied to a patient and/or surface hardness. Additionally or alternatively, the sensors may also be able to determine a temperature of a patient. In certain embodiments, the sensors can be used to sense finger position, recognize objects and/or recognize real-time hand activity including vector of force applied. In yet other embodiments, additional sensors may be included on the surface of the provider device, which may detect the presence of bacteria on the provider device.

The sensors 301-303 may be located at various positions on/within the glove 305. For example, one or more sensors may be situated on or about the index finger distal phalanx, the middle finger distal phalanx, the thumb distal phalanx and/or on the palm area of the glove 305.

In one embodiment, the sensors 301-303 may comprise a lightweight, thin, and/or flexible material. For example, the sensors may comprise a piezoresistive material disposed between two pieces of flexible polyester, with printed silver conductors on each inner half. In one specific embodiment, A401 FLEXI-FORCE tactile sensors manufactured by Tekscan, Inc. may be employed.

The provider device may comprise additional electronics 310, which may be in electrical communication with the sensors (e.g., via electrical wiring). For example, the provider device will typically include a receiver and/or transceiver 306 and a power source 307. Optionally, the provider device 300 may also include a processor 304 and/or an output module 308.

In one embodiment, the provider device 300 is adapted to transmit pressure information detected by the sensors to the server and/or one or more user devices. To that end, the provider device may include a receiver and/or transceiver 306 comprising a wireless communications circuit that employs Bluetooth, BLE, NFC, RFID, ZIGBEE, Z Wave, Wi-Fi, or cellular link (e.g., CDMA or GSM) technology. The transceiver 306 may send/receive transmissions that are encrypted and/or asynchronous.

In one specific embodiment, the transceiver 306 may utilize Bluetooth technology adapted for power-saving and scaled-down data transmissions. The Bluetooth transceiver may be a Parani-ESD 300D (Sena Technologies Inc., San Jose, Calif.) with an operating supply voltage of 3.3 V.

The provider device may comprise a processor 304, such as a general-purpose microprocessor, special-purpose microprocessor, and/or any other kind of central processing unit ("CPU"). Generally, the processor 304 may modulate, condition, convert, and/or record the received pressure information. In one embodiment, as the physician applies a force to a location on the patient's body, the processor 304 receives the pressure information from the sensors as an analog signal, and converts this signal to a digital signal. The digital signal may then be sent to the server and/or a user device via the transceiver 306.

In certain embodiments, the processor 304 may be the MCF51JM128VLH (Freescale Semiconductor Inc., West Austin, Tex.). This commercialized device is a 32-bit reduced instruction set computing (RISC) microprocessor and an ultralow power microcontroller. It operates at processor core speeds up to 50.33 MHz. The operating supply voltage is between 2.7 V and 5.5 V.

The provider device may optionally comprise memory 309 in communication with the processor 304, such as but not limited to, ROM (e.g., NAND flash, NOR flash, flash on another processor, other solid-state storage, mechanical or optical disks) and/or RAM. The memory may store any information described herein, such as but not limited to sensor information. In one embodiment, flash memory may be used for its desirable shock resistant characteristics and ability to retain stored data without the need for an active power source.

In one embodiment, the pressure information processed by processor 304 may be employed to display a notification via output 308. The output 308 may comprise a visible LED light, a display screen, a sound, a vibration, etc. The output may indicate a range of pressure exerted by the provider and/or may alert the provider that a desired pressure is being exerted.

The provider device 300 may comprise one or more power sources 307 that can be utilized to power the electrical components thereof. In certain embodiments, the provider device may comprise a removable and/or rechargeable power source, such as a rechargeable battery. In one embodiment, the provider device may be powered by a lithium-ion battery, which may be adapted for at least eight hours of data collection. In other embodiments, the provider device may be powered by nickel metal hydride cell batteries.

It will be appreciated that the provider device 300 typically comprises a device ID, such as a MAC address or other unique ID, which may be employed to distinguish the provider device from any other devices that may also send/receive messages to/from the server and/or user device(s).

It will be further appreciated that, although shown to comprise a glove 305, the provider device 300 is not limited to such embodiments. For example, the provider device may be a handheld device that may be used by the provider to apply pressure to a patient during a pain measurement session.

In one alternative embodiment, the provider device 300 comprises a cylindrical housing and a soft tip. Such embodiment may be employed by a provider to apply pressure to any number of locations on a patient's body during one or more pain measurement sessions. Specifically, the provider may contact a patient with the soft tip of the device. In this way, the provider device will allow providers to focus an exam onto specific points on a patient's body and will assist operators who are unable or otherwise prefer not to use a glove-type provider device.

It will be appreciated that this embodiment of the provider device may comprise any of the electrical components described above with respect to the glove-type provider device shown in FIG. 3. For example, the provider device may comprise a number of sensors located about the tip (i.e., disposed within the tip or on the outer surface thereof). The sensors may determine pressure applied to a patient and/or surface hardness. Additionally or alternatively, the sensors may also be able to determine a temperature of a patient.

Body-Mapping System

Figure 4:
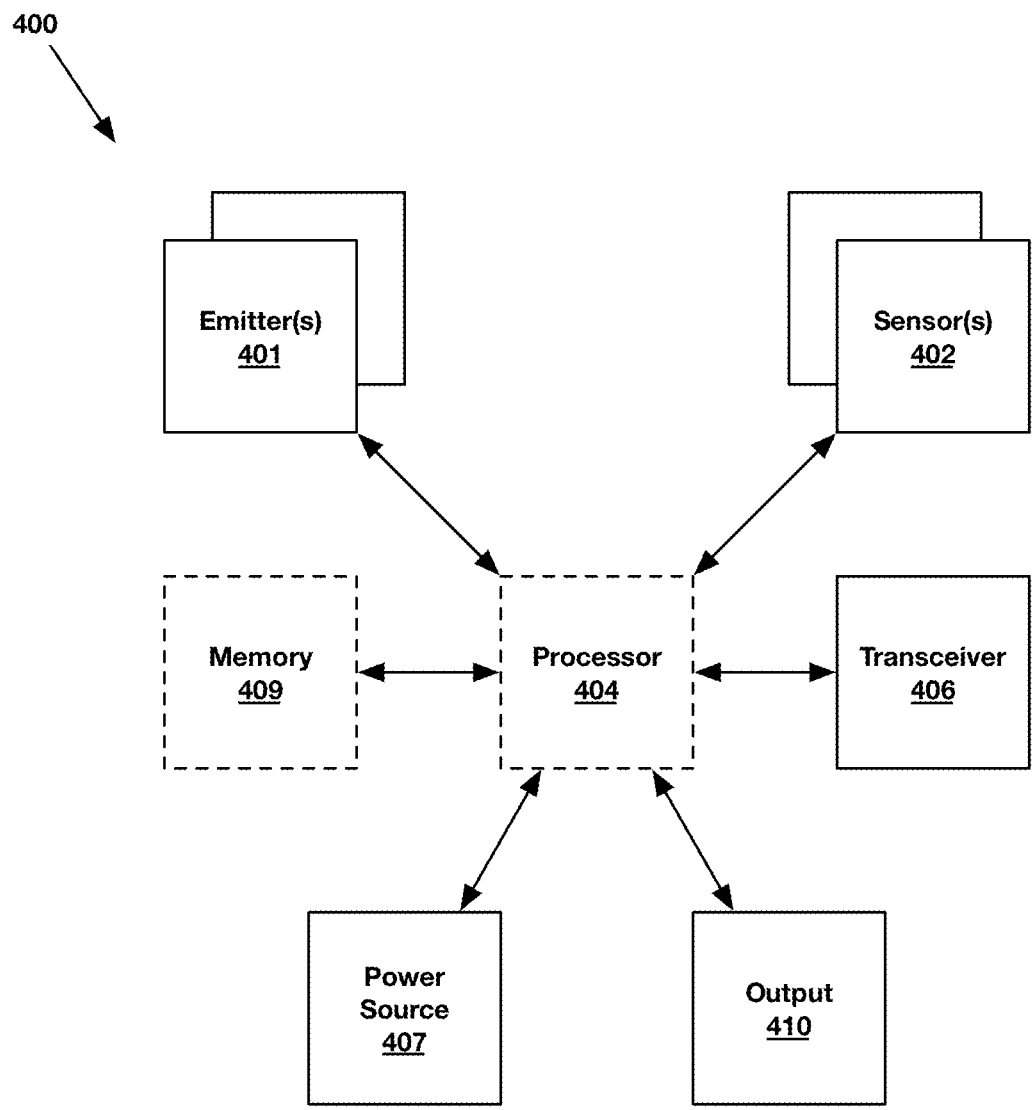
FIG. 4 shows an exemplary body-mapping system 400 in accordance with one or more embodiments presented herein.

Referring to FIG. 4, a block diagram of an exemplary body-mapping system 400 is illustrated. Generally, the body-mapping system 400 determines location information relating to a location on a patient's body to which a provider applies pressure during a pain measurement session (i.e., location information) and transmits such information to the server and/or a user device. In certain embodiments where a referred pain device is employed (discussed below), the body-mapping system 400 may also determine referred pain information relating to locations on a patient's body to/through which pain travels when pressure is applied to a particular area. Such referred pain location information may also be transmitted to the server and/or user device.

As shown in FIG. 4, the body-mapping system 400 may comprise a number of emitters 401 and sensor(s) 402. The emitter(s) 401 may project a pattern of spots onto the scene and the sensor(s) 402 may capture an image of the projected pattern. The system may then compute the 3D coordinates of points in the scene (including points on the surface of the patient's and/or provider's body) by triangulation, for example, based on transverse shifts of the spots in the pattern. This approach is advantageous in that it does not require the patient nor provider to hold or wear any sort of beacon, sensor, or other marker. It provides the depth coordinates of points in the scene relative to a predetermined reference plane, at a certain distance from the emitter(s)/sensor(s).

Alternatively, the system may use other methods of 3D mapping that use projected spot patterns (which may be uncorrelated or possibly more regular grid-based patterns), such as stereoscopic imaging or time-of-flight measurements, based on single or multiple cameras or other types of sensors, as are known in the art.

Additionally or alternatively, the sensors may further include a camera to detect one or more colors (e.g., red, green and/or blue). The camera may be employed to record a session and/or to construct a 2D or 3D representation of the patient. As discussed below, such camera may be employed to determine referred pain location information via a referred pain device.

The emitter(s) 401 and sensor(s) 402 may be employed by the body-mapping system to create depth maps, or a representation of a scene as a 2D matrix of pixels, in which each pixel corresponds to a respective location in the scene and has a respective pixel depth value, indicative of the distance from a certain reference location to the respective scene location. A depth map generally has the form of an image in which the pixel values indicate topographical information, rather than brightness and/or color of the objects in the scene.

It will be appreciated that the body-mapping system may employ any of a number of different methods and systems for creating such depth maps. Depth maps may be created, for example, by detection and processing of an image of an object onto which a pattern of spots is projected. Depth mapping methods using these sorts of projected patterns are described, for example, in PCT International Publications WO 2007/043036, WO 2007/105205, WO 2008/120217, and WO 2010/004542, whose disclosures are incorporated herein by reference.

In some embodiments, depth maps may be processed in order to segment and identify objects in the scene, such as various locations on a patient's body and/or various features of a provider's hand. For example, the body-mapping system may employ a method in which a depth map is segmented so as to find a contour of a humanoid body, as described in PCT International Publication WO 2007/132451 (incorporated herein by reference in its entirety). The contour may be processed in order to identify a torso and one or more limbs of the body. An input is generated to control an application program running on a computer by analyzing a disposition of at least one of the identified limbs in the depth map.

As another example, the body-mapping system may employ a method for processing a temporal sequence of depth maps of a scene containing a humanoid form, as described in U.S. Patent Application Publication 2011/0052006 (incorporated herein by reference in its entirety). At least one depth map may be processed so as to find a location of the head of the humanoid form, and dimensions of the humanoid form may be estimated based on this location. Moreover, the system may track movements of the humanoid form over a sequence of depth maps using the estimated dimensions.

In one embodiment, the body-mapping system may employ a method for depth mapping, as described in U.S. Patent Application Publication 2014/0118335 (incorporated herein by reference in its entirety). Such method may include receiving an image of a pattern of spots that has been projected onto a scene that includes a patient and/or a hand of a provider. The image may be processed in order to segment and find a 3D location of the provider's hand. The spots appearing on the patient's body and/or hand of the provider in the 3D location may be connected in order to extract separate, contours of such objects.

In yet other embodiments, the body-mapping system may employ various wireless communication protocols to determine location information via signal triangulation or other means. Exemplary protocols include, but are not limited to, Global Positioning System ("GPS") equipment, cellular networks (e.g., CDMA, GSM, LTE, etc.) and/or Wi-Fi networks.

In one embodiment, the body-mapping system is adapted to transmit location information detected by the sensors to the server and/or one or more user devices. To that end, the body-mapping system may include a receiver and/or transceiver 406 comprising a wireless communications circuit, such as Bluetooth, BLE, NFC, RFID, ZIGBEE, Z Wave, Wi-Fi, or cellular link (e.g., CDMA or GSM). The transceiver 406 may send/receive transmissions that are encrypted and/or asynchronous.

The body-mapping system typically comprises a processor 404, such as a general-purpose microprocessor, special-purpose microprocessor, and/or any other kind of CPU. Generally, the processor 404 may modulate, condition, convert, analyze and/or record the received visual data in order to determine location information.

The processor may employ artificial intelligence machine-learning algorithms to map the received visual data to models representing people of different backgrounds (e.g., age, height, gender, body type, clothing and more). In one embodiment, the processor 404 receives the visual data from the sensors 402 as an analog signal, and converts this signal to a digital signal representing location information.

In certain embodiments, the body-mapping system may further comprise an output 410. In one such embodiment, the output 410 may comprise a 3D topographical map of the general outlines of a patient with the depth, location, and time/date of pressure also displayed. In other embodiments, the output may additionally or alternatively comprise magnetic resonance images which may further comprise sagittal and/or coronal views.

The body-mapping system 400 may optionally comprise memory 409 in communication with the processor 404, such as but not limited to, ROM (e.g., NAND flash, NOR flash, flash on another processor, other solid-state storage, mechanical or optical disks) and/or RAM. The memory may store any information described herein, such as but not limited to visual data and/or location information.

The body-mapping system 400 may comprise one or more power sources 407 that can be utilized to power the electrical components thereof. In certain embodiments, the system may comprise a removable and/or rechargeable power source, such as a rechargeable battery.

In certain embodiments, the body-mapping system 400 may involve non-contact position measurement devices for tracking hand movements. For example, the system may comprise position measurement devices that are magnetic, ultrasonic, optical, etc. In other embodiments (not shown), the body-mapping system 400 may include a bodysuit comprising sensors that is worn by the patient.

Patient Device

Figure 5:
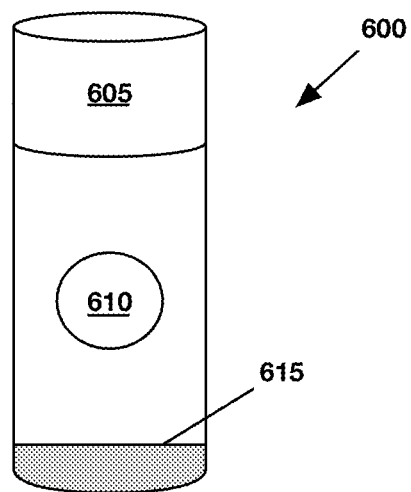
FIG. 5 shows an exemplary patient device 600 in accordance with one or more embodiments presented herein.
Figure 6:
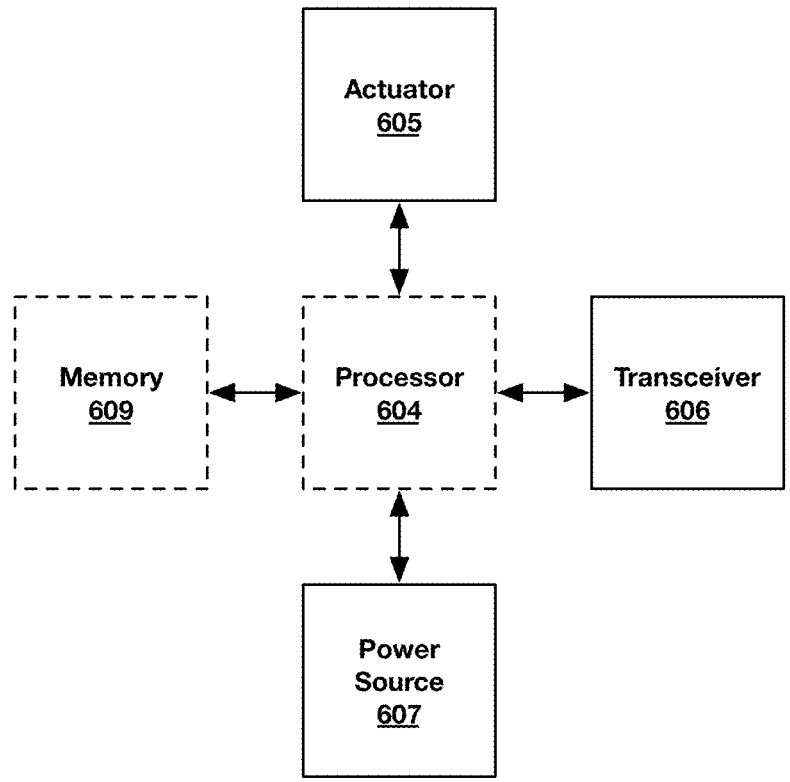
FIG. 6 shows a block diagram of the exemplary patient device 600 of FIG. 5 in accordance with one or more embodiments presented herein.

Referring to FIGS. 5 and 6, an exemplary patient device 600 is illustrated. Generally, the patient device 600 may be adapted to receive feedback information from a patient representing an indication of the intensity of pain experienced by the patient at any given time during a pain measurement session.

As shown, the patient device 600 comprises an actuator 605 that may be activated by a patient upon experiencing pain. In certain embodiments, the actuator 605 may comprise a button or lever that is pushed or squeezed by the patient. The patient may push/squeeze the actuator with various amounts of force to indicate the amount of pain they are experiencing. For example, the patient may lightly push/squeeze the actuator 605 to indicate that they are experiencing a small amount of pain and the patient may push/squeeze the actuator with more force to indicate that they are experiencing a larger amount of pain. In certain embodiments, the amount of force applied to the actuator may be directly proportional to the amount of pain experienced by the patient.

In alternative embodiments, the input actuator 605 may be modified based on individual patient circumstances, such as disabilities. For example, the actuator 605 may comprise a pedal, a biting mechanism, a muscle-clenching mechanism, a facial-expression-reading mechanism, a verbal-output-reading mechanism, etc. In other embodiments, the actuator may comprise a plurality of buttons wherein each button corresponds to a different pain intensity. And, in yet other embodiments, the feedback information may be manually entered by a provider (e.g., via a client application running on a user device).

In one embodiment, the patient device 600 is adapted to transmit feedback information to the server and/or one or more user devices. To that end, the patient device 600 may include a receiver and/or transceiver 606 comprising a wireless communications circuit, such as Bluetooth, BLE, NFC, RFID, ZIGBEE, Z Wave, Wi-Fi, or cellular link (e.g., CDMA or GSM). In one specific embodiment, the transceiver 606 may utilize Bluetooth technology adapted for power-saving and scaled-down data transmissions. The transceiver 606 may send/receive transmissions that are encrypted and/or asynchronous.

The patient device may comprise a processor 604, such as a general-purpose microprocessor, special-purpose microprocessor, and/or any other kind of CPU. Generally, the processor 604 may modulate, condition, convert, and/or record the information received from the actuator 605. In one embodiment, as the patient activates the actuator, the processor 604 receives an analog signal, and converts this signal to a digital signal. The digital signal may then be transmitted to the server and/or a user device via the transceiver 606.

The patient device may optionally comprise memory 609 in communication with the processor 604, such as but not limited to, ROM (e.g., NAND flash, NOR flash, flash on another processor, other solid-state storage, mechanical or optical disks) and/or RAM. The memory may store any information described herein, such as but not limited to feedback information. In one embodiment, flash memory may be used for its desirable shock resistant characteristics and ability to retain stored data without the need for an active power source.

In one embodiment, information relating to the feedback information processed by processor 604 may be displayed via output 610. The output 610 may comprise a visible LED light, a display screen, a speaker, a vibration motor, etc. The output may correspond directly to the force exerted on the actuator, and such output may be employed to alert the provider that a certain intensity of pain is being experienced by the patient.

The patient device 600 may comprise one or more power sources 607 that can be utilized to power the electrical components thereof. In certain embodiments, the patient device may comprise a removable and/or rechargeable power source, such as a rechargeable battery. In one embodiment, the patient device may be powered by a lithium-ion battery, which may be adapted for at least eight hours of data collection. In other embodiments, the patient device may be powered by nickel metal hydride cell batteries.

It will be appreciated that the patient device 600 typically comprises a device ID, such as a MAC address or other unique ID, which may be employed to distinguish the patient device from any other devices that may also send/receive messages to/from the server and/or user device(s).

It will be further appreciated that, although shown as a handheld device that may be gripped by a patient, the patient device 600 may comprise other forms, as desired or required. For example, the patient device may be a mouth-, hip-, foot- or knee-operated device.

In certain embodiments, a referred pain device 615 may be integrated into, or otherwise included with, the patient device 600 in order to map referred pain. The device 615 may be adapted to receive referred pain information from a patient, wherein the referred pain information represents an indication of the location(s) on a patient's body where pain is experienced at any given time during a pain measurement session.

In one embodiment, the patient may use the referred pain device 615 to demonstrate, on their own body, how the sensation of pain travels from an operators point of stimulation (e.g., the location where a provider device contacts the patient) to a final destination of the referred pain. For example, the patient may trace their body with the referred pain tracking device, starting from the point of stimulation and ending at the most distal expression of referred pain.

As shown in FIG. 5, a referred pain device 615 may be integrated into, or otherwise included with, the patient device 600. For example, the referred pain device 615 may comprise a metal, plastic, or cloth material that can be identified by the body-mapping system. Such material may comprise a bright color to facilitate recognition by the body-mapping system.

In other embodiments, a separate referred pain device may be employed. Such device may comprise a wearable or holdable device that is detectable by the body-mapping system. For example, the tracking device may comprise a fingertip cover adapted to fit about a patient's fingertip, wherein the cover may be made of a brightly colored cloth or plastic material.

As another example, a tracking device may comprise a metal or plastic pointer-shaped device having a tip. The tip of such device may comprise a brightly colored material such that it can be identified by the mapping system.

Body Map

Figure 7:
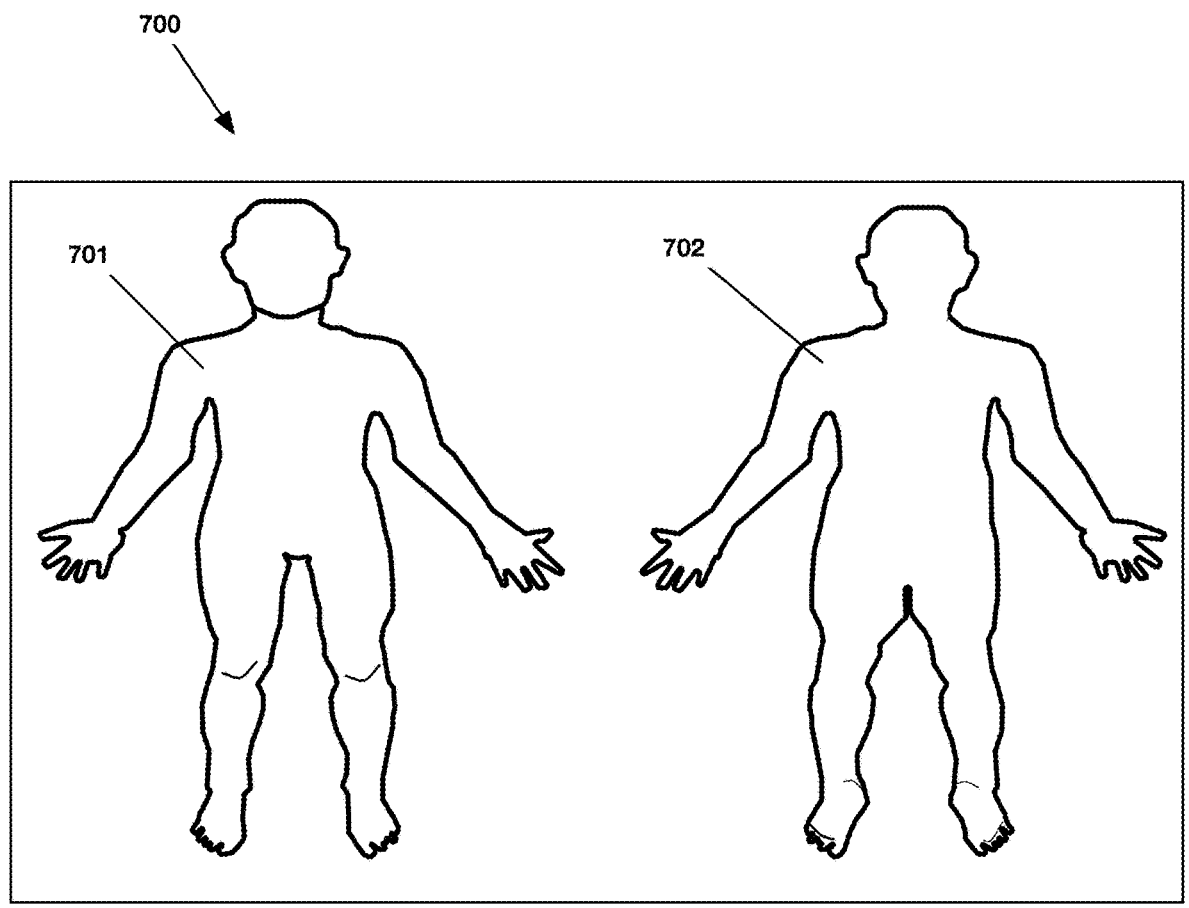
FIG. 7 shows an exemplary body map 700 in accordance with one or more embodiments presented herein.

Referring to FIG. 7, an exemplary body map 700 with a front view 701 and a back view 702 of a patient is shown. In one embodiment, the body map may comprise a 3D, topographical map of the general outlines of a patient with the depth, location, and time/date of pressure also displayed. The front view 701 and back view 702 may further comprise location of pain indications, location of internal organs, blood veins and vessels. In other embodiments, the body map may additionally or alternatively comprise magnetic resonance images which may further comprise sagittal and/or coronal views.

In one embodiment, a body map 700 may be superimposed onto a radiological study (e.g., an X-ray or MRI) to see if there is correspondence between symptoms and radiologic findings for a wide range of illnesses like chronic neck or back pain, chronic abdominal pain, etc. Accordingly, the embodiments described herein may help clinicians more accurately match the pain that patients report with radiological studies.

In certain embodiments, the body map may include generalized anatomy details. For example, the body map may display one or more of: bones, muscles, ligaments, major nerves and/or major arteries.

Rectal Probe Device

Figure 8:
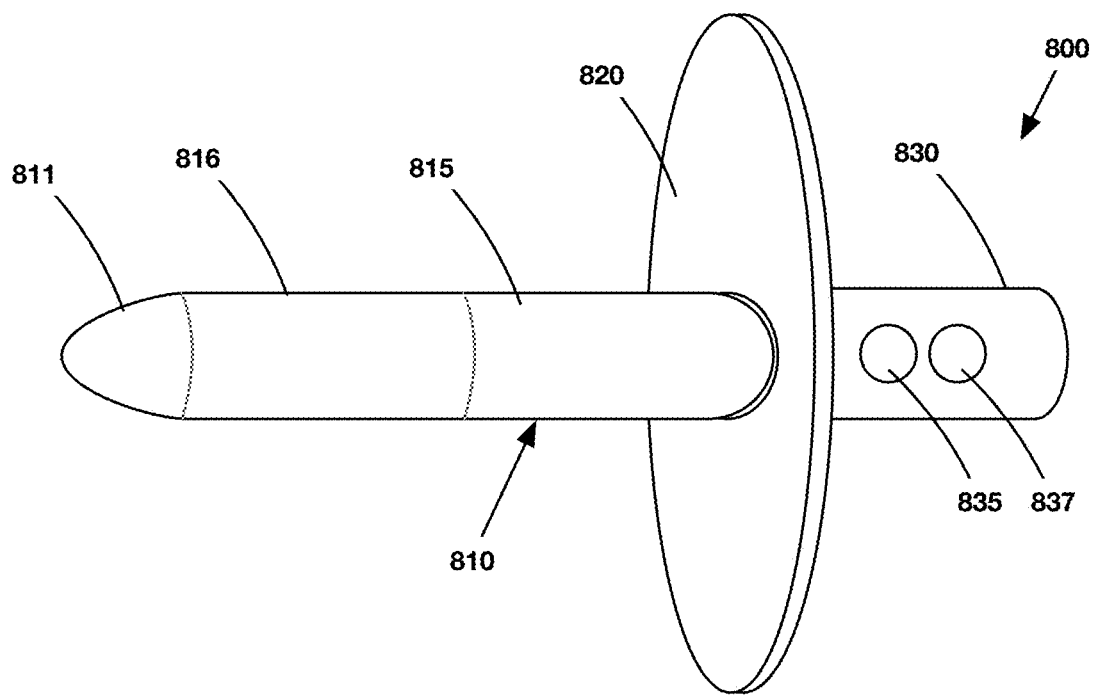
FIG. 8 shows an exemplary rectal probe device 800 in accordance with one or more embodiments presented herein.
Figure 9:
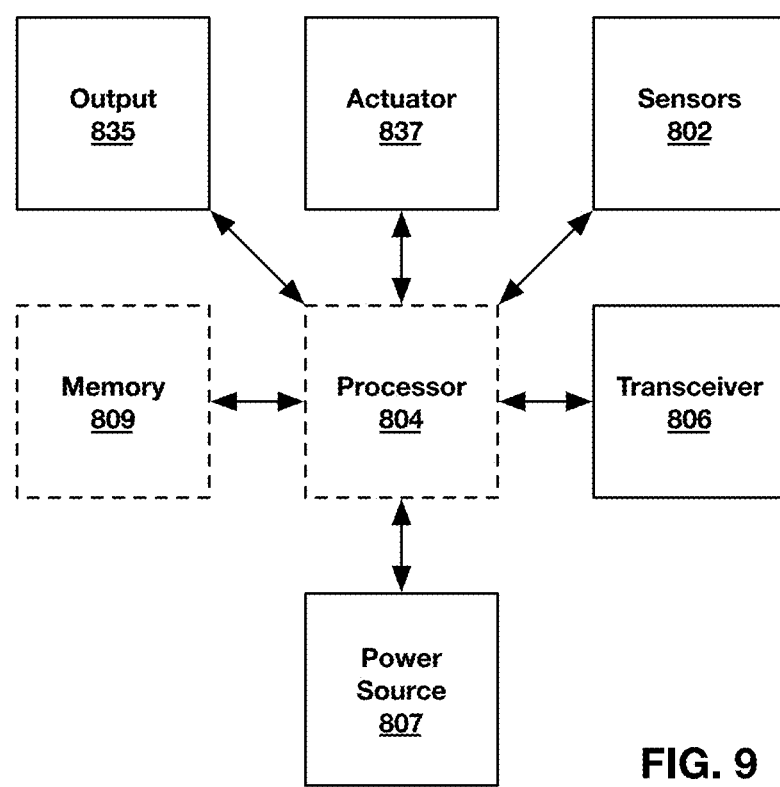
FIG. 9 shows a block diagram of an exemplary rectal probe device 800 of FIG. 8 in accordance with one or more embodiments presented herein.

Referring to FIGS. 8 and 9, an exemplary rectal probe device 800 is illustrated. Generally, the rectal probe device 800 may be employed during a pain assessment session to measure rectal sphincter muscle tone. Such information may assist providers and researchers in identifying connections between pain perception and rectal tone at initiation of pain perception and/or as pain perception changes with various applied therapies.

In certain embodiments, the rectal probe device 800 may additionally or alternatively be employed to apply pressure to a patient's sphincter muscles. For example, light pressure may be applied during a therapy session in order to assist patients who need help transitioning from sympathetic distress (i.e., trauma response) to parasympathetic relaxation (i.e., de-traumatization).

In one embodiment, the rectal probe device 800 comprises a handle 830, a base 820, and an insertion probe 810. The handle 830 may be shaped such that it can be held by a practitioner during use. And the base 820 may be flared to ensure correct entry depth and internal alignment of the insertion probe 810.

As shown, the insertion probe 810 comprises a substantially cylindrical housing 815 extending from the base 820 of the probe to an insertion end 811. The insertion end 811 may comprise a rounded and/or tapered shape and a diameter that is less than that of the housing 815 to allow for ease of entry.

As shown, the housing 815 may be in communication with an inflatable balloon 816 or similar mechanism to allow for the diameter of the probe to be increased/decreased via inflation/deflation of the balloon. To that end, the inflatable balloon 816 may extend around the housing 815 and may comprise a sealable aperture. Although not shown, a tube may extend from the aperture to a mechanical or electrical pump, which may be used to inflate/deflate the balloon 816. In certain embodiments, the balloon may be made from a silicone or rubber material.

Generally, the insertion probe 810 may comprise a length of from about 5 cm to about 15 cm. When the inflatable balloon 816 is deflated, the insertion probe 815 may comprise a diameter of from about 0.5 cm to about 2.5 cm (e.g., about 1 cm, about 1.5 cm, about 2 cm or about 2.5 cm). In certain embodiments, the inflatable balloon 816 may be inflated to increase the diameter of the insertion probe by about 1 mm to about 5 mm (distributed uniformly in all directions).

As shown in FIG. 9, the rectal probe device 800 may comprise a number of sensors 802. Such sensors 802 may be located at various positions on/within the housing 815, from the insertion end 811 to the base 820 thereof. The sensors may determine rectal sphincter muscle tone via measuring the pressure of such muscles upon insertion of the probe. Additionally or alternatively, the sensors may also be able to determine a temperature of a patient.

The rectal probe device 800 may comprise additional electronics housed within the housing 815, the base 820 and/or the handle 830. Such electronics may be in electrical communication with the sensors (e.g., via electrical wiring). For example, the device will typically include a receiver and/or transceiver 806 and a power source 807. Optionally, the device may also include a processor 804 and/or an output module 835.

In one embodiment, the rectal probe device 800 is adapted to transmit sensor and/or sphincter muscle tone information detected by the sensors to the server and/or one or more user devices. To that end, the device 800 may include a receiver and/or transceiver 806 comprising a wireless communications circuit that employs Bluetooth, BLE, NFC, RFID, ZIGBEE, Z Wave, Wi-Fi, or cellular link (e.g., CDMA or GSM) technology. The transceiver 806 may send/receive transmissions that are encrypted and/or asynchronous.

The rectal probe device 800 may comprise a processor 804, such as a general-purpose microprocessor, special-purpose microprocessor, and/or any other kind of CPU. Generally, the processor 804 may modulate, condition, convert, and/or record the received sensor and/or sphincter muscle tone information. In one embodiment, the processor 804 receives such information from the sensors 802 as an analog signal, and converts this signal to a digital signal. The digital signal may then be sent to the server and/or a user device via the transceiver 806.

The rectal probe device may optionally comprise memory 809 in communication with the processor 804, such as but not limited to, ROM (e.g., NAND flash, NOR flash, flash on another processor, other solid-state storage, mechanical or optical disks) and/or RAM. The memory 809 may store any information described herein, such as but not limited to sensor information and/or sphincter muscle tone information. In one embodiment, flash memory may be used for its desirable shock resistant characteristics and ability to retain stored data without the need for an active power source.

In one embodiment, the information processed by the processor 804 may be employed to display a notification via an output 835, such as visible LED light, a display screen, a sound, a vibration, etc. The output 835 may indicate a range of pressure and/or may alert one or more users (e.g., a provider and/or a patient) of a specific pressure. In one particular embodiment, the output 835 may comprise sound from a tone generator that gives a variable tone calibrated to a pressure reading. In another embodiment, the output 835 may comprise a display that shows pressure information in number format and/or graphically. In yet another embodiment, a secondary pressure device may wrap around a finger of a patient, and such secondary pressure device may mimic the pressure of the rectal sphincter (i.e., the rectal sphincter tone information) in real time.

The rectal probe device 800 comprises one or more actuators 837 that may be activated by a user in order to turn the device on/off and/or to inflate and/or deflate the device. In certain embodiments, the actuator 837 may comprise a button or lever that is pushed or squeezed by the user.

The rectal probe device 800 may comprise one or more power sources 807 that can be utilized to power the electrical components thereof. In certain embodiments, the device may comprise a removable and/or rechargeable power source, such as a rechargeable battery. In one embodiment, the device may be powered by one or more lithium-ion batteries or nickel metal hydride cell batteries.

It will be appreciated that the rectal probe device 800 typically comprises a device ID, such as a MAC address or other unique ID, which may be employed to distinguish the rectal probe device from any other devices that may also send/receive messages to/from the server and/or user device(s).

Methods of Operation

Figure 10:
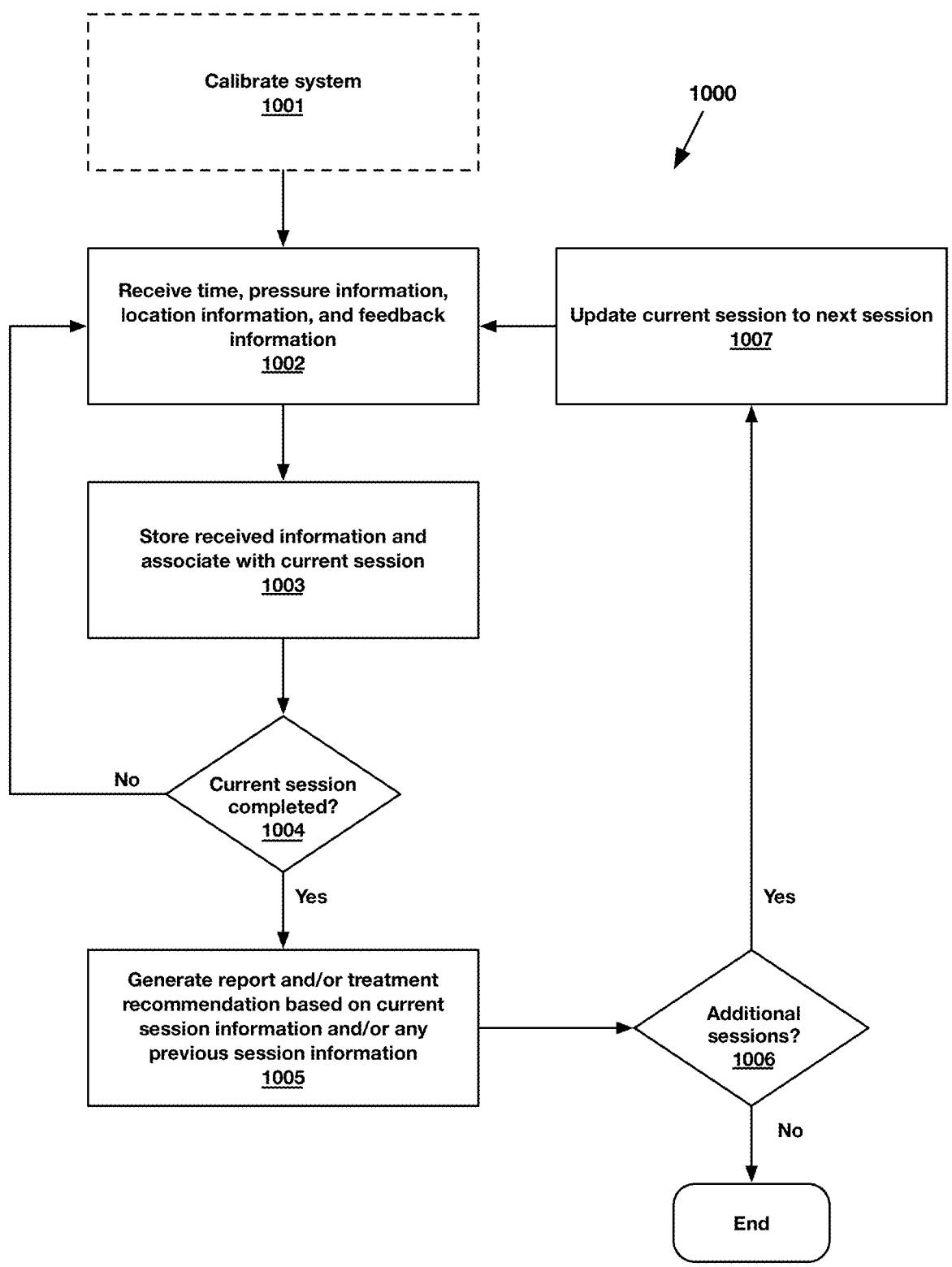
FIG. 10 shows an exemplary method 1000 for determining and characterizing pain in accordance with one or more embodiments presented herein.

Referring to FIG. 10, an exemplary method 1000 for detecting and characterizing pain is provided. The method may begin with an optional calibration process 1001, whereby a standard or predetermined amount of stimuli (e.g., manual pressure, electrical, cold, sharp) is provided to a patient in specific anatomical sites and feedback information is received (e.g., via a patient device). The received feedback information may be used to calibrate the patient's non-verbal expression of pain from exam to exam and/or in comparison to other patients (e.g., for a research protocol).

At step 1002, a first session begins when a provider applies a first pressure to a first location on a patient's body at a first time and first feedback information is received by the server. As discussed above, first pressure information may be determined by a provider device and transmitted to the server. First location information may be determined by a body-mapping system and transmitted to the server. And the first feedback information may be received by a patient device and transmitted to the server.

It will be appreciated that additional session information may also be received by the server. For example, a temperature sensor in the provider device may determine a first temperature at the first location and may transmit such temperature information to the server. As another example, the body-mapping system may determine a patient's position (which may change throughout a given session and/or across multiple sessions) and the system may transmit such information to the server. As yet another example, the body-mapping system may determine referred pain information (e.g., by determining a position of a referred pain tracking device) and the system may transmit such information to the server. And, as another example, a rectal probe may determine sphincter muscle tone information and transmit the same to the server.

At step 1003, the session information received by the server at step 1002 may be stored (e.g., in a database) and associated with the current session. Such session information may also include patient information relating to the patient and/or provider information relating to the provider.

At step 1004, a determination may be made as to whether the current session has ended. For example, a provider may indicate that a given session is over and/or the system may determine that a predetermined amount of time has elapsed since the session started. If the current session has not ended, the method may return to step 1002 to receive additional session information for the current session. Otherwise, the method may proceed to step 1005.

At step 1005, a report may be generated based on any of the current session information. In one embodiment, the report may comprise a graphical representation of the session information, such as a 2D or 3D body map. Generally, the report may be stored by the system and transmitted to one or more user devices such that it may be viewed by a user.

A treatment recommendation may additionally or alternatively be determined at step 1005. Such treatment recommendation may be based on the current session information and may comprise, for example, one or more recommended medications, exercises, stretches, and/or changes to a daily routine of the patient (e.g., diet, sleep, etc.). The treatment recommendation may be stored by the server, associated with the current session and/or transmitted to one or more user devices. Optionally, the treatment recommendation may be included in, or otherwise provided with, a generated report.

In certain embodiments, the current session information may be compared to any previous session information at step 1005. Such comparison may be employed to generate a new or updated report, determine a new or updated treatment recommendation, determine efficacy of a particular treatment, and/or determine whether a patient is accurately reporting their symptoms.

In any event, the method may continue on to step 1006, where a determination may be made as to whether the current session is the last session. Generally, the method may end after a predetermined number of sessions, upon achieving a desired patient outcome (e.g., reduction of pain), or as desired or required by the patient or the provider.

If the current session is the last session, the method may end. Otherwise, the method may proceed to step 1007 by updating the current session to the next session. The method then returns to step 1002 where session information is received for the updated current session.

It will be appreciated that one or more steps of the above method may be repeated as desired or required. For example, a provider may apply a second pressure to a second location on the patient's body at a second, later time during the first session. And the server may receive: second feedback information from the patient device, second pressure information from provider device, and second location information from body-mapping system.

Expanding on this example, the provider may apply a third pressure to a third location on the patient's body at a third time during a second session. And the server may receive second session information comprising: third feedback information from the patient device, third pressure information from provider device, and third location information from body-mapping system. In this case, the method may include one or more of: generating a report and/or treatment recommendation based on the first session information; generating a report and/or treatment recommendation based on the second session information; and/or generating a report and/or treatment recommendation based on a comparison of the second session information to the first session information.

In certain cases, the system may assist the practitioner in determining the efficacy of a particular treatment. For example, a practitioner may provide a treatment to a user between a first session and a second session. The system may then compare the session information of the first session to the session information of the second session in order to determine how the treatment affected the patient. Additionally, the system may provide an updated treatment recommendation based on such comparison. It will be appreciated that this iterative process may be repeated as desired or required.

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

All references including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:

1. A system comprising:
a provider device operated by a provider, the provider device adapted to measure pressure information relating to a force applied, via the provider device, to a location on a body of a patient;
a patient device operated by the patient, the patient device comprising:
an actuator adapted to be actuated by the patient via application of an amount of force that corresponds to an intensity of pain experienced by the patient due to the force applied to the patient by the provider device;
a processor in communication with the actuator, the processor adapted to determine feedback information relating to the intensity of pain experienced by the patient, based on the amount of force applied to the actuator; and
a referred pain device adapted to be used by the patient to indicate referred pain information relating to one or more additional locations on the patient's body where the patient experiences pain due to the applied force;
a body-mapping system adapted to:
determine location information relating to the location of the applied force; and
detect the referred pain information; and
a server in communication with the provider device, the body-mapping system and the patient device via a network, the server adapted to:
receive the pressure information from the provider device;
receive the location information and the referred pain information from the body-mapping system;
receive the feedback information from the patient device;
store, in a memory, pain information comprising the pressure information, the location information, the referred pain information and the feedback information; and
generate a report comprising a graphical representation of the pain information.

2. A system according to claim 1, wherein the pressure information comprises a magnitude of the applied force, a start time of the applied force and an end time of the applied force.

3. A system according to claim 2, wherein the location information comprises one or more of the group consisting of: a direction of the applied force, an area over which the force is applied to the location and a depth within the location to which the force is applied.

4. A system according to claim 3, wherein the report comprises a two-dimensional ("2D") or three-dimensional ("3D") body map.

5. A system according to claim 1, wherein the server is further adapted to determine a treatment recommendation for the patient based on the pain information, the treatment recommendation relating to one or more of the group consisting of: a medication, an exercise, a stretch, a diet and sleep.

6. A system according to claim 1, wherein the provider device comprises:
a glove adapted to be worn on a hand of the provider; and
a pressure sensor disposed within an interior of the glove or on a surface thereof, the pressure sensor adapted to measure the pressure information.

7. A system according to claim 6, wherein:
the provider device is further adapted to measure temperature information relating to a temperature of the location;
the provider device further comprises a temperature sensor adapted to measure the temperature information;
the server is further adapted to receive the temperature information; and
the pain information further comprises the temperature information.

8. A system according to claim 6, wherein the provider device further comprises an output adapted to display an indication relating to the pressure information.

9. A system according to claim 1, wherein the patient device further comprises a housing adapted to be gripped in a hand of the patient.

10. A system according to claim 1, wherein the body-mapping device comprises:
one or more emitters adapted to project a pattern of spots onto the patient's body;
one or more sensors adapted to capture an image of the projected pattern; and
a processor adapted to:
receive the image; and
determine the location information based on the image.

11. A system according to claim 1, wherein:
the body-mapping device is further adapted to determine position information relating to a position of the patient when the force is applied;
the server is further adapted to receive the position information from the body-mapping system; and
the pain information further comprises the position information.

12. A system according to claim 1, wherein the referred pain device comprises a colored cloth or plastic material that is detectable by the body-mapping device.

13. A system according to claim 1, further comprising a user device in communication with the server via the network, wherein:
the user device is adapted to receive patient information relating to the patient, the patient information comprising one or more of: identification information, consent information, billing information, insurance information, medical information and historical pain information; and the server is further adapted to:
receive the patient information from the user device;
store the patient information in the memory; and
determine a treatment recommendation for the patient based on the pain information and the patient information, the treatment recommendation relating to one or more of the group consisting of: a medication, an exercise, a stretch, a diet and sleep.

14. A system according to claim 13, wherein:
the user device is further adapted to receive a pain measurement session plan comprising one or more of: a target pressure, a target location and a target duration; and the server is further adapted to:
receive the pain measurement session plan; and
store the pain measurement session plan in the memory; and
transmit a notification to the provider device and/or the user device, based on a comparison of the pain information to the pain measurement session plan.

\* \* \* \* \*